United States Patent
Liphardt et al.

(10) Patent No.: US 7,057,717 B1
(45) Date of Patent: Jun. 6, 2006

(54) SYSTEM FOR AND METHOD OF INVESTIGATING THE EXACT SAME POINT ON A SAMPLE SUBSTRATE WITH AT LEAST TWO WAVELENGTHS

(75) Inventors: Martin M. Liphardt, Lincoln, NE (US); Blaine D. Johs, Lincoln, NE (US); Craig M. Herzinger, Lincoln, NE (US); Ping He, Lincoln, NE (US); Christopher A. Goeden, Lincoln, NE (US); John A. Woollam, Lincoln, NE (US); James D. Welch, Omaha, NE (US)

(73) Assignee: J.A. Woollam Co., INC, Lincoln, NE (US)

( * ) Notice: Subject to any disclaimer, the term of this patent is extended or adjusted under 35 U.S.C. 154(b) by 317 days.

(21) Appl. No.: 10/426,590

(22) Filed: Apr. 30, 2003

Related U.S. Application Data

(63) Continuation-in-part of application No. 10/050,802, filed on Jan. 15, 2002, now Pat. No. 6,859,278, and a continuation-in-part of application No. 09/583,229, filed on May 30, 2000, now Pat. No. 6,804,004.

(60) Provisional application No. 60/405,858, filed on Aug. 26, 2002.

(51) Int. Cl.
*G01N 21/00* (2006.01)

(52) U.S. Cl. .................................. 356/237.2
(58) Field of Classification Search .............. None
See application file for complete search history.

(56) References Cited

U.S. PATENT DOCUMENTS

| | | | |
|---|---|---|---|
| 5,078,513 A | 1/1992 | Spaulding et al. | 385/14 |
| 5,091,801 A | 2/1992 | Ebstein | 359/665 |
| 5,864,436 A | 1/1999 | Noyes | 359/785 |
| 5,963,327 A * | 10/1999 | He et al. | 356/369 |
| 5,973,846 A | 10/1999 | McConica | 359/642 |
| 6,590,708 B1 * | 7/2003 | Nakai et al. | 359/558 |

* cited by examiner

*Primary Examiner*—Tu T. Nguyen
(74) *Attorney, Agent, or Firm*—James D. Welch

(57) ABSTRACT

Disclosed are system for and method of analyzing the substantially the exact same point on a sample system with at least two wavelengths, or at least two ranges of wavelengths for which the focal lengths do not vary more than within an acceptable amount.

10 Claims, 6 Drawing Sheets

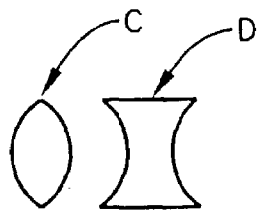
FIG. 1_f  FIG. 1_g
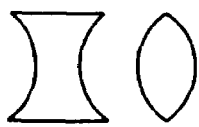
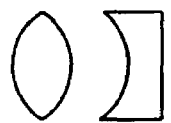   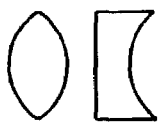   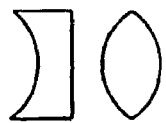   
FIG. 1_h   FIG. 1_i   FIG. 1_j   FIG. 1_k
         
FIG. 1_l   FIG. 1_m   FIG. 1_n   FIG. 1_o
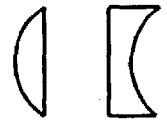   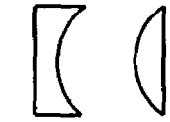   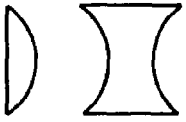   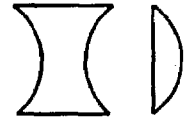
FIG. 1_p   FIG. 1_q   FIG. 1_r   FIG. 1_s
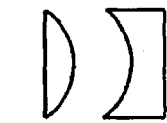   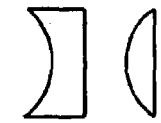   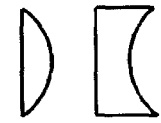   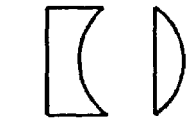
FIG. 1_t   FIG. 1_u   FIG. 1_v   FIG. 1_w
```
C   D   C   D                C   D   D   C
     FIG. 1_x                     FIG. 1_y
D   C   D   C                D   C   C   D
     FIG. 1_z                     FIG. 1_zz
```

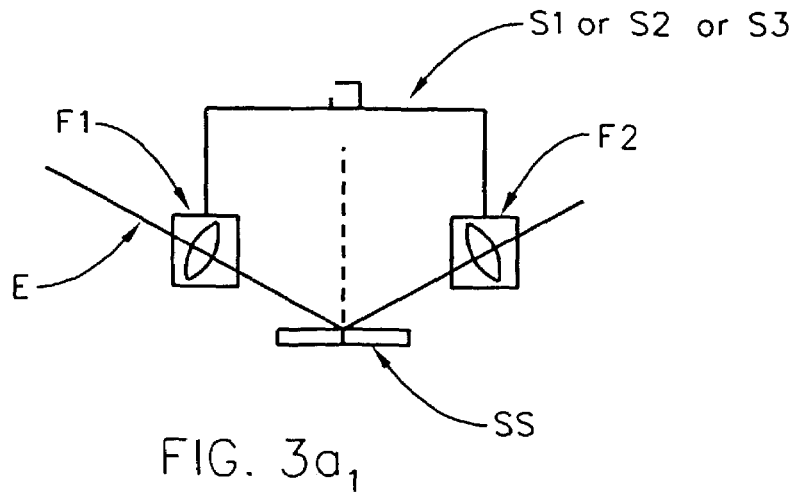
FIG. 3a₁
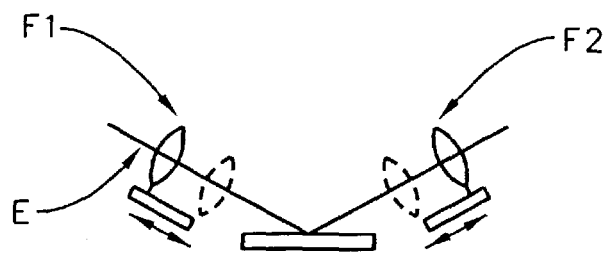
FIG. 3a₂
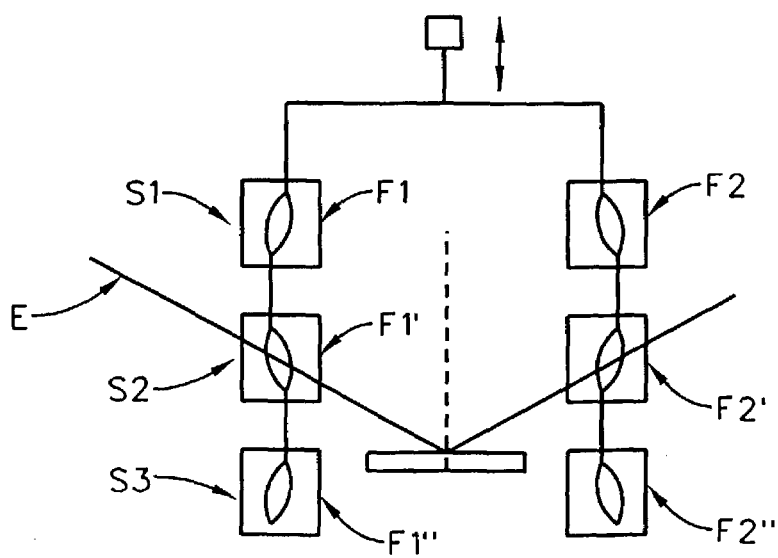
FIG. 3a₃

SYSTEM FOR AND METHOD OF INVESTIGATING THE EXACT SAME POINT ON A SAMPLE SUBSTRATE WITH AT LEAST TWO WAVELENGTHS

Specification, This Application is a CIP of Applications Ser. Nos. 10/050,802 Filed Jan. 15, 2002, now U.S. Pat. No. 6,859,278 and Ser. No. 09/583,229 Filed May 30, 2000, now U.S. Pat. No. 6,804,004 and Claims benefit of Provisional Application Ser. No. 60/405,858 Filed Aug. 26, 2002.

TECHNICAL FIELD

The disclosed invention relates to the use of electromagnetic radiation to investigate sample systems, and more particularly to a method of analyzing the exact same point on a sample system with at least two wavelengths.

BACKGROUND

It is known to investigate sample systems with electromagnetic radiation by application of ellipsometers, polarimeters, reflectometers, spectrophotometers and the like. Prior art describes the use of lenses to focus a beam of electromagnetic radiation onto a sample and to recollimate it thereafter, and known Patent Applications describe use of focusing and/or collimating "Achromatic" Lenses before and/or after a sample. Ideally an "Achromatic" lens provides the same focal length at all wavelengths in a beam of electromagnetism, however, practical "Achromatic" Lenses have focal lengths which vary with wavelength, in a cyclic manner about an average. That is, a plot of Focal Length vs. Wavelength rises and falls such that a line drawn substantially parallel to the Wavelength Axis passes through said plot a plurality of times. At said Focal Length then at least two, and typically more, wavelengths for which the Focal length is the same are identified. Achromatic Lenses can be designed to set two desired wavelengths, (eg. 193 nm and 248 nm), and often others will also result, on a determined, non-selected basis, at which the Focal Lengths are equal.

In ellipsometry it is often desirable to take data which pertains to at least two selected wavelengths, and it is also important to investigate a sample with said multiple wavelengths at exactly the same spot thereupon as well as detect resulting data for each wavelength similarly. This requires equal source and detector side focal lengths at said wavelengths.

The disclosed invention then is a system of lenses which are designed to have equal focal lengths at a plurality of wavelengths, and a method of their use in analyzing a specific spot on a sample using electromagnetic radiation applied at an oblique angle.

Another aspect of the disclosed invention is that a plurality of lens sets can be designed which provide different combinations of wavelengths at which focal lengths are equal, and said plurality of sets of lenses can be mounted in, for instance an ellipsometer system, to allow them to be sequentially positioned in the path of an electromagnetic beam, so that more wavelengths can be sequentially caused to focus on the same spot on a sample.

In another variation, a single lens can be mounted so that it can be moved toward and away from a sample, so as to sequentially cause different wavelengths to focus on the same spot on a sample at different wavelengths.

It is also noted that supplementing a minimal number of wavelengths with increased number of angles-of-incidence can provide sufficient data sets where necessary.

A search of Patents provide:

Patent to Ebstein, U.S. Pat. No. 5,091,801 which describes a nearly index matched optic formed of at least two elements for adjusting focal lengths;

a Patent to Noyes, U.S. Pat. No. 5,864,436 which describes an objective lens which has the same focal length at two wavelengths;

a Patent, U.S. Pat. No. 5,973,846 to McConica which describes an auto focus system for a digital camera which has the focus of two spectra offset from one another; and a Patent, U.S. Pat. No. 5,078,513 to Spaulding et al., which describes a lens in a waveguide of an integrated optical waveguide which is corrected for chromatic dispersion.

Even in view of the prior art, a need remains for improved ellipsometer, polarimeter, reflectometer, spectrophotometer and the like systems which include lenses that provide the same focal length at least two wavelengths.

DISCLOSURE OF THE INVENTION

A disclosed invention method of analyzing a sample at the exact same spot with at least two wavelengths of electromagnetic radiation, comprises the steps of: practicing steps a and b in either order, said steps a and b being:

a) providing a selection from the group consisting of:
ellipsometer;
polarimeter;
spectrophotometer; and
reflectometer;

which sequentially comprises a source of polychromatic electromagnetic radiation, a stage for supporting a sample and a detector;

b) providing a two lens system which has been designed to provide focal lengths which are substantially exactly the same at two specified wavelengths;

c) placing one of said lenses provided in step b prior to a sample which is positioned on said stage for supporting a sample, and one of said after said sample, each of said lenses being placed a focal length distance from a specific point on said sample;

d. causing polychromatic electromagnetic radiation from said source thereof to become focused onto said sample by said pre-sample lens, such that two wavelengths are focused onto said sample at substantially exactly the same point thereupon;

e) utilizing only data obtained at said wavelengths for which the focal lengths are substantially the same in sample analysis.

Said method of analyzing a sample at the exact same spot can include steps a–d being repeated using a second lens system which is designed to provide the same substantially equal focal length at at least two wavelengths, at least one of said at least two wavelengths being different from the two wavelengths provided by the lens systems provided in step b, and wherein step e additionally utilizes data obtained at said additional at least two wavelengths in said sample analysis.

A modified recital of the method of analyzing a sample at the exact same spot with at least two wavelengths of electromagnetic radiation, comprising the steps of:

practicing steps a and b in either order, said steps a and b being:

a) providing a selection from the group consisting of:
ellipsometer;
polarimeter;

spectrophotometer; and
reflectometer;

which sequentially comprises a source of polychromatic electromagnetic radiation, a stage for supporting a sample and a detector;
  b) providing:
    b1) a first set of two lenses which have been designed to provide focal lengths which are substantially exactly the same at two specified wavelengths; and
    b2) a second set of two lenses which have been designed to provide focal lengths which are substantially exactly the same at two specified wavelengths, at least one of said wavelengths being different than the two wavelengths in the first set of lenses provided in step b1;
  c) placing one of said lenses provided in step b1 prior to a sample which is positioned on said stage for supporting a sample, and one of said lenses provided in step b1 after said sample, each of said lenses being placed a focal length distance from a specific point on said sample;
  d. causing polychromatic electromagnetic radiation from said source thereof to become focused onto said sample by said pre-sample lens, such that said two wavelengths are focused onto said sample at substantially exactly the same point thereupon, such that via reflection from said sample said two wavelengths are entered into said detector;
  e) placing one of said lenses provided in step b2 prior to a sample which is positioned on said stage for supporting a sample, and one of said lenses provided in step b1 after said sample, each of said lenses being placed a focal length distance from a specific point on said sample;
  f) causing polychromatic electromagnetic radiation from said source thereof to become focused onto said sample by said pre-sample lens, such that said two wavelengths are focused onto said sample at substantially exactly the same point thereupon, such that via reflection from said sample said two wavelengths are entered into said detector;
  g) analyzing said sample utilizing only data provided by said detector based upon said wavelengths for which the focal lengths of the lenses provided in steps b1 and b2 are substantially the same.

It is also within the scope of the disclosed invention to allow the focal lengths at said two wavelengths to vary a bit, within an acceptable range. In that case the method of analyzing a sample at the exact same spot with at least two wavelengths of electromagnetic radiation, comprises the steps of:

practicing steps a and b in either order, said steps a and b being:
  a) providing a selection from the group consisting of:
    ellipsometer;
    polarimeter;
    spectrophotometer; and
    reflectometer;

which sequentially comprises a source of polychromatic electromagnetic radiation, a stage for supporting a sample and a detector;
  b) providing two lens systems which have been designed to provide ranges of wavelengths in Focal Length vs. Wavelength plots, for which wavelengths in said ranges of wavelengths the focal lengths are centered about two intended specified wavelengths, variance in said focal lengths being within an acceptable range;
  c) placing one of said lens systems provided in step b prior to a sample which is positioned on said stage for supporting a sample, and one of said lens systems after said sample, each of said lens systems being placed a focal length distance from a specific point on said sample;
  d. causing polychromatic electromagnetic radiation from said source thereof to become focused onto said sample by said pre-sample lens system, such that said ranges of wavelengths around said two wavelengths are focused onto said sample at substantially exactly the same point thereupon.
  e) utilizing only data obtained at said wavelengths for which the focal lengths are within acceptable ranges of deviation from being substantially the same, in sample analysis.

Again, said method can involve analyzing the sample at the exact same spot in which steps a–d are repeated using additional lens systems which are designed to provide substantially the same equal focal lengths at at least two additional wavelengths, using lenses which are designed to provide ranges of substantially equal focal lengths around at least two additional wavelengths, at least one of said two additional wavelengths being different from the two wavelengths provided by the lenses provided in the first practice of step b.

A modified method of analyzing a sample at the exact same spot with at least two wavelengths of electromagnetic radiation, comprising the steps of:

practicing steps a and b in either order, said steps a and b being:
  a) providing a selection from the group consisting of:
    ellipsometer;
    polarimeter;
    spectrophotometer;
    reflectometer; and
    functional equivalent;

which sequentially comprises a source of polychromatic electromagnetic radiation, a stage for supporting a sample and a detector;
  b) providing a set of two lenses which have been designed to provide a first focal length which is substantially exactly the same at first and second specified wavelengths, and a second focal length which is substantially exactly the same at third and forth specified wavelengths; and
  c) placing one of said lenses provided in step b prior to a sample which is positioned on said stage for supporting a sample, and one of said lenses provided in step b after said sample, each of said lenses being placed a focal length distance from a specific point on said sample;
  d) causing polychromatic electromagnetic radiation from said source thereof to become focused onto said sample by said pre-sample lens, such that said first and second wavelengths are focused onto said sample at substantially exactly the same point thereupon, such that via reflection from said sample said two wavelengths are entered into said detector;
  e) causing said lenses to be moved toward or away from said sample such that the said third and forth wavelengths are focused onto said sample at substantially exactly the same point thereupon as was investigated in step d, such that via reflection from said sample said two wavelengths are entered into said detector;
  f) causing polychromatic electromagnetic radiation from said source thereof to become focused onto said sample by said pre-sample lens, such that said two wavelengths are focused onto said sample at substantially exactly the same point thereupon, such that via reflection from said sample said two wavelengths are entered into said detector;
  g) analyzing said sample utilizing only data provided by said detector based upon said first, second, third and forth wavelengths.

A disclosed invention system can be described as being selected from the group consisting of:
ellipsometer;
polarimeter;
spectrophotometer;
reflectometer;
and functionally similar systems;
which sequentially comprises a source of polychromatic electromagnetic radiation, a stage for supporting a sample and a detector. Said system being characterized by lens systems which have been designed to provide focal lengths which are substantially exactly the same at two specified wavelengths, one of said lens systems being placed prior to a sample which is positioned on said stage for supporting a sample, and one of said lens systems after said sample, each of said lens systems being placed a focal length distance from a specific point on said sample.

As a specific example, the disclosed invention can also be considered to be an ellipsometer system sequentially comprising elements selected from the group consisting of:
a. a Source of a spectroscopic beam electromagnetic radiation;
b. a Polarizer element;

in either order elements c. and d.:
c. optionally a compensator element;
d. (additional element(s));
e. a material system;

in either order elements f. and g.:
f. (additional element(s));
g. optionally a compensator element;
h. an Analyzer element; and
i. a Detector System;

in which said additional elements in d. comprise selection(s) from the group consisting of:
beam directing means;
input lens(es); and
window(s);

in which said additional elements in f. comprise selection(s) from the group consisting of:
beam directing means;
output lens(es); and
window(s);

at least one of said input and output lenses, when selected and present, being of multi-element construction, wherein, for said at least one of said input and output lenses at least two elements thereof are made from different materials, such that in use the focal length for each wavelength in a range of wavelengths is essentially the same as that for every other wavelength, wherein said additional elements are selected from the group consisting of:
both demonstrating birefringence;
neither demonstrating birefringence;
one demonstrating birefringence and the other not;

said two sequentially oriented lens systems each having exactly the same focal length at two wavelengths.

The disclosed invention can be characterized as a lens system with application in ellipsometer and polarimeter systems wherein birefringence, and spectroscopic electromagnetic beam spot size chromatic dispersion reduction and focal length chromatic dispersion reduction is desired, said lens system comprising at least two sequentially oriented elements, one of said two sequentially oriented elements being of a shape and orientation which individually converges a beam of electromagnetic radiation caused to pass therethrough, and the other being of a shape and orientation which individually diverges a beam of electromagnetic radiation caused to pass therethrough, wherein said convergence effect is greater than said divergence effect; there being a region between said at least two elements such that, in use, a beam of electromagnetic radiation sequentially passes through one of said at least two elements, then said region therebetween, and then the other of said at least two elements before emerging as an effectively converged, focused, beam of electromagnetic radiation; said lens system being characterized in that the focal lengths at two or three wavelengths are exactly the same.

The disclosed invention can be described as a dual stage lens system with application in ellipsometer systems, said dual stage lens system comprising two sequentially oriented lens systems, each of said two sequentially oriented lens systems being comprised of:
at least two sequentially oriented lens elements, one of said at least two sequentially oriented lens elements being of a shape and orientation which individually converges a beam of electromagnetic radiation caused to pass therethrough, and the other being of a shape and orientation which individually diverges a beam of electromagnetic radiation caused to pass therethrough, there being a region between said at least two lens elements such that, in use, a beam of electromagnetic radiation sequentially passes through one of said at least two lens elements, then said region therebetween, and then the other of said at least two lens elements before emerging as a focused beam of electromagnetic radiation; said dual stage lens system comprising at least two sequentially oriented lens elements being a selection from the group consisting of:
a sequential combination of a converging element, a diverging element, a converging element and a diverging element;
a sequential combination of a converging element, a diverging element, a diverging element and a converging element;
a sequential combination of a diverging element, a converging element, a diverging element and a converging element;
a sequential combination of a diverging element, a converging element, a converging element and a diverging element.

said two sequentially oriented lens systems each having exactly the same focal length at two wavelengths.

In general the lense systems typically presents with said a converging element selected from the group consisting of:
a bi-convex;
a plano-convex with an essentially flat side;

and presents with said diverging element selected from the group consisting of:
a bi-concave lens element;
a plano-concave with an essentially flat side.

Further, said lens systems typically comprise a selection from the group consisting of:
a) a sequential combination of a bi-convex element and a bi-concave element;
b) a sequential combination of a bi-concave element and a bi-convex element;
c) a sequential combination of a bi-convex element and a plano-concave element with said concave side of said piano-concave element adjacent to said bi-convex element;

d) a sequential combination of a bi-convex element and a plano-concave element with said essentially flat side of said plano-concave element being adjacent to said bi-convex element;
e) a sequential combination of a plano-concave element and a bi-convex element with said essentially flat side of said plano-concave element adjacent to said bi-concave element;
f) a sequential combination of a plano-concave element and bi-convex element with said concave side of said plano-concave element adjacent to said bi-convex element;
g) a sequential combination of a plano-convex element and a bi-concave element with said essentially flat side of said plano-convex element adjacent to said bi-concave element;
h) a sequential combination of a bi-concave element with a plano-convex element with said convex side of said plano-convex element adjacent to said bi-concave element;
i) a sequential combination of a plano-concave element and a plano-convex element with the essentially flat side of said plano-concave element being adjacent to the convex side of the plano-convex element;
j) a sequential combination of a plano-concve element and a plano-convex element with the essentially flat side of said planoconcave element being adjacent to the convex side of said plano-convex element;
k) a sequential combination of a plano-convex element and a plano-concave element with the essentially flat side of said plano-covex element and the essentially flat side of said plano-concave element being adjacent to one another;
l) a sequential combination of a plano-concave element and a plano-convex element with the concave side of said plano-concave element being adjacent to the convex side of the plano-convex element;
m) a sequential combination of a plano-convex element and a bi-concave element with said convex side of said plano-convex element adjacent to said bi-concave element;
n) a sequential combination of a bi-concave element and a plano-convex element with said essentially flat side of said plano-convex element adjacent to said bi-concave element;
o) a sequential combination of a plano-convex element and a plano-concave element with said convex side of said plano-convex element adjacent to the concave side of the plano-concave element;
q) a sequential combination of a plano-concave element and a plano-convex element with said essentially flat side of said plano-convex element being adjacent to the essentially flat side of the plano-concave element;
r) a sequential combination of a plano-convex element and a plano-concave element with said convex side of said plano-convex element being adjacent to the essentially flat side of the plano-concave element;
s) a sequential combination of a plano-concave element with a plano-convex element with the essentially flat side of said plano-convex element being adjacent to the concave side of said plano-concave element;

and wherein said region between said at least two elements has essentially the optical properties of a selection from the group consisting of:
a void region; and
a functional equivalent to a void region.

And further yet, each of said at least two elements is typically made of a material independently selected from the group consisting of:
$CaF_2$;
$BaF_2$;
$LiF$;
$MgF_2$; and
fused silica;

and wherein each of said at least two elements are individually selected to be made of different materials. One embodiment, for instance, provides lens systems wherein one of said at least two lens elements in each of said two sequentially oriented lenses is made of $CaF_2$ and the other element in each of said two sequentially oriented lenses is made of fused silica.

It is also noted that the focal length of said lens systems is often selected to be between forty and forty-one millimeters, based on practical ellipsometer system dimensions.

The invention will be better understood by reference to the Detailed Description Section of theis Disclosure, in combination with the Drawings.

SUMMARY

It is therefore a purpose and/or objective of the disclosed invention to teach a system for and method of analyzing, via use of electromagnetic radiation, substantially the exact same point on a sample system with at least two wavelengths, or at least two ranges of wavelengths for which the focal lengths do not vary more than within an acceptable amount.

It is another purpose and/or objective of the disclosed invention to disclose use of multi-element lenses which are ground to provide the exact same focal length at two selected wavelengths.

It is yet another purpose and/or objective of the disclosed invention to disclose use of a plurality of systems, each of which comprise multi-element lenses which are ground to provide the exact same focal length at two selected wavelengths, with the wavelengths involved being different in the different systems.

Other purposes and/or objectives will become apparent by a reading of the Specification and claims.

BRIEF DESCRIPTION OF THE DRAWINGS

FIGS. 1f–1w show various multi-element lens configurations which can provide quais-achromatic focal length vs. wavelength.

FIGS. 1x–1zz show sequences in multi-lens configurations.

FIG. 3a1 demonstrates a basic ellipsometers systems comprising lenses F1 and F2 in input and output sides of a sample system. Said F1 and F2 can be in a slidable S1, S2 or S3 as shown in FIGS. 3b abd 3c, which slides into and out of the paper.

FIG. 3a2 indicates that a system can be constructed to allow moving a single lens toward or away from a sample.

FIG. 3a3 shows another approach to providing a sequence of lenses (F1) (F1') (F1") and (F2) (F2') and (F2") into the beam (E) of elelctromagnetic radiation.

DETAILED DESCRIPTION

Figure 1A:
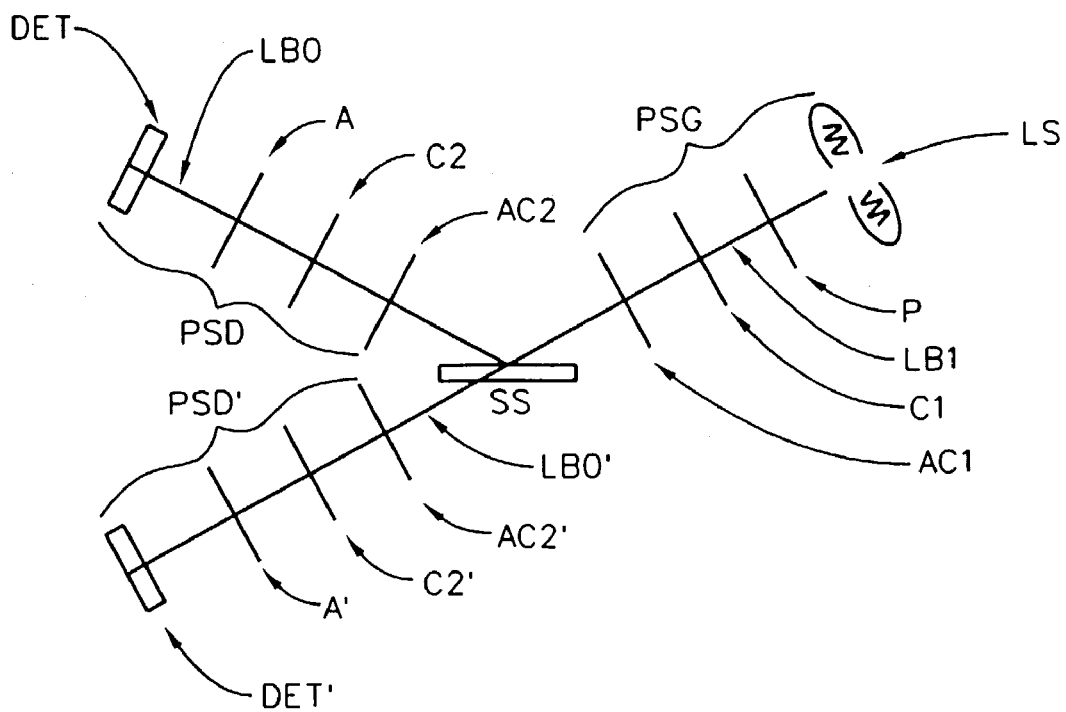
FIG. 1a demonstrates an ellipsometer system with both reflection and transmission pathways indicated.

Turning now to the Drawings, FIG. 1a demonstrates an ellipsometer or polarimeter system with both reflection and transmission pathways indicated. Note there is s Polarization State Generator (PSG) which comprises a Source of Electromagnetic Radiation (LS), a Polarizer (P), a Compensator (C1), Additional Element (AC1) which for the purposes of this disclosure can be considered to be a focusing lens, such as identified as (F1) in FIG. 1b. Also shown are Reflection and Transmission Mode Polarization State Detector Systems (PSD) (PSD') which each comprise Additional Elements (AC2) (AC2'), Compensator (C2) (C2'), Analyzer (A) (A'), and Detector (DET) (DET'). Note the the Additiona Component (AC2) can be considered a Focusing Lens, such as (F2) in FIG. 1b. In use the Source of Electromagnetic Radiation (LS) provides a (polychromatic) beam of electromagnetic radiation which is provided a polarizations atate by Polarizer (P) and Compensator (C1), then is focused into Sample (SS) by Additional Element (AC1). After interaction with the Sample System (SS) the beam enters Polarization State Detector (PSD) (PSD'). It is noted that the Compensators (C1) (C2) (C2') can be eliminated.

Figure 1B:
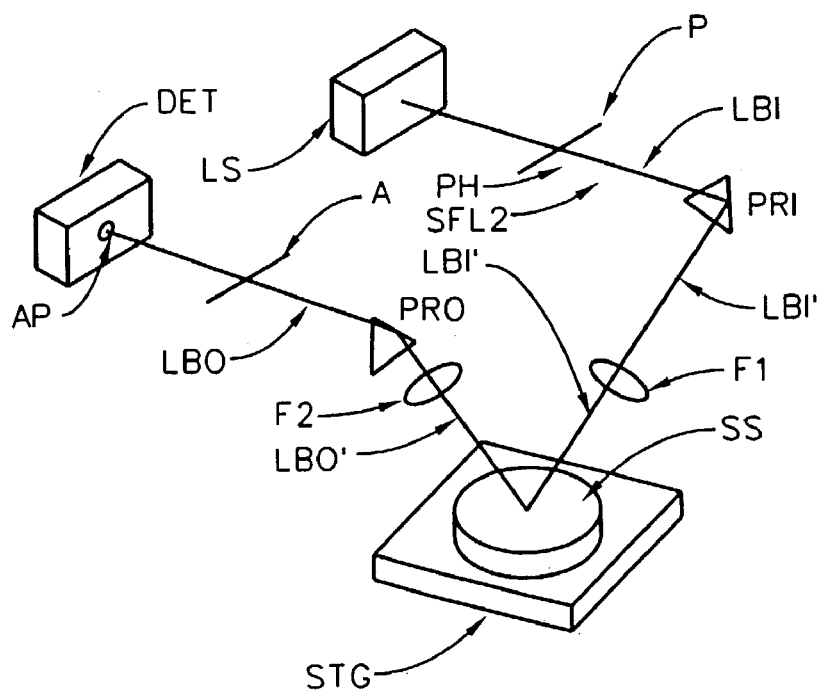
FIG. 1b shows an alternative reflection mode ellipsometer system.
Figure 1C:
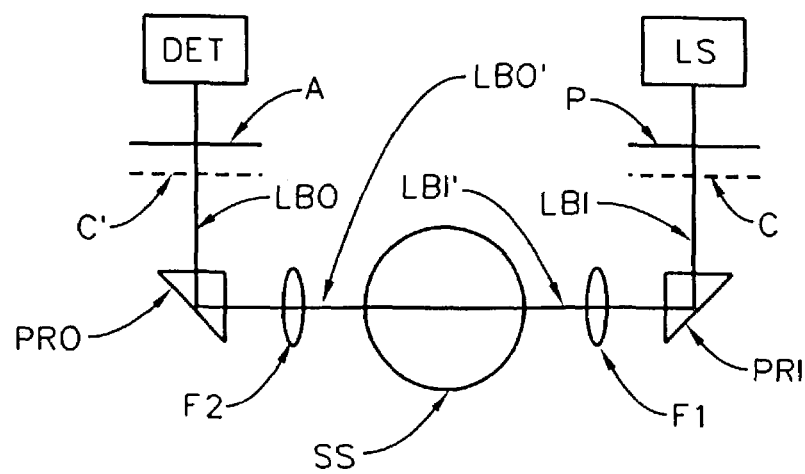
FIG. 1c shows a top view of the FIG. 1b ellipsometer system.

FIG. 1b shows a Reflection Mode variation on the System shown in FIG. 1a. Shown are a Source of Electromagnetic Radiation (LS), a Polarizer (P), a First Reflective Means (PRI), a Focusing Lens (F1), a Sample System (SS) on a Stage (STG), a Colimating Lens (F2) a Second Reflective Means (PRO), an Analyzer (A) and a Detector (DET) which provides entry thereinto via an Aperture (A). FIG. 1c shows a top view of the System of FIG. 1b. It is noted that (PRI) and (PRO) can be made of the same material, but the preferred embodiment provides that (PRI) be made of BK7 (refractive index approximately 1.55) and that (PRO) be made of F2 (refractive index approximately 1.7).

Figure 1D:
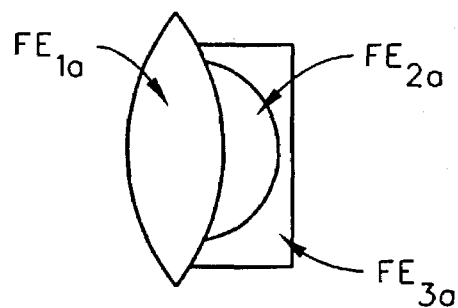
FIGS. 1d and 1e demonstrate single and multiple stage multi-element lens systems which provide quasi-achromatic focal lengths and spot sizes.
Figure 1E:
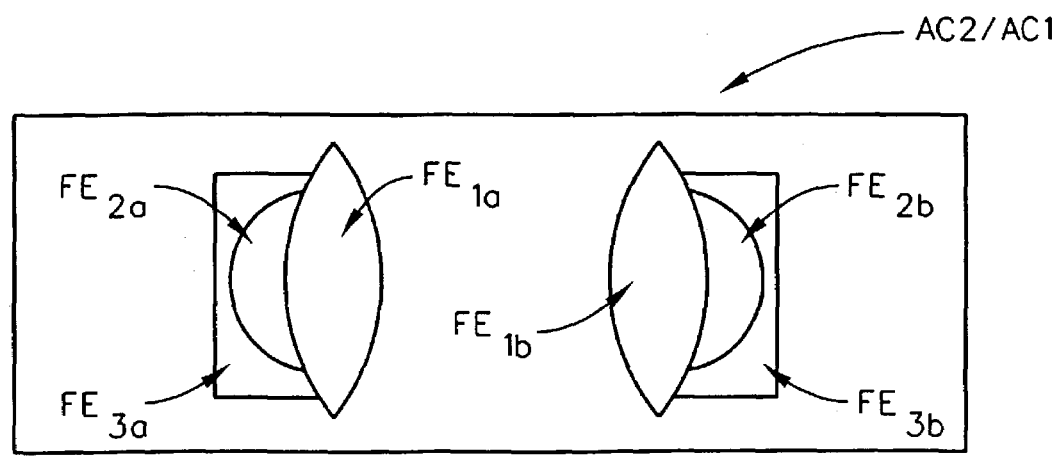

FIG. 1d shows a Lens comprised of multiple elements $(FE_{1a})$, $(FE_{2a})$ and $(FE_{3a})$. FIG. 1e shows a sequential two Lens System in which the First Lens comprises $(FE_{3a})$, $(FE_{2a})$ and $(FE_{1a})$ and in which the Second Lens comprises $(FE_{1b})$, $(FE_{2b})$ and $(FE_{3b})$. The purpose of multi-element lenses is to provide more achromatic characteristics than is possible with single element lenses.

FIGS. 1f–1w are included to provide insight to various FIG. 1d Single Multi-Element Lens configurations, and FIGS. 1x–1zz are included to show that FIG. 1e two lense systems can be constructed of alternating Converging (C), (eg. the First Lens Element in FIG. 1f), and Diverging (D), (eg. the Second Element in FIG. 1f), lenses in any functional order. It is not the purpose of this Disclosure to describe any specific Lens construction, but rather to provide insight as to general Multiple Element Lens constructions, the Elements of which can be ground to provide exactly the same Focal Length at two selected wavelengths. A present invention lens system, which is particularly well suited for application in ellipsometer systems, then provides for spectroscopic electromagnetic beam spot size and focal length chromatic dispersion reduction by configuring at least two sequentially oriented elements, one of said at least two sequentially oriented elements being of a shape and orientation which individually converges a beam of electromagnetic radiation caused to pass therethrough, and the other being of a shape and orientation which individually diverges a beam of electromagnetic radiation caused to pass therethrough, there being a region between said first and second elements such that, in use, a beam of electromagnetic radiation sequentially passes through said first element, then said region therebetween, and then said second element before emerging as a focused beam of electromagnetic radiation. Such a lens system with application in ellipsometer systems is characterized by a converging element which presents as a selection from the group consisting of:

a bi-convex;

a plano-convex with an essentially flat side;

and said diverging element is characterized as a selection from the group consisting of:

a bi-concave lens element;

a plano-concave with an essentially flat side.

Further, as shown in FIGS. 1f–1w, said present invention lens systems can comprise a selection from the group consisting of:

a) a sequential combination of a bi-convex element and a bi-concave element;

b) a sequential combination of a bi-concave element and a bi-convex element;

c) a sequential combination of a bi-convex element and a plano-concave element with said concave side of said plano-concave element adjacent to said bi-convex element;

d) a sequential combination of a bi-convex element and a plano-concave element with said essentially flat side of said plano-concave element being adjacent to said bi-convex element;

e) a sequential combination of a plano-concave element and a bi-convex element with said essentially flat side of said plano-concave element adjacent to said bi-concave element;

f) a sequential combination of a plano-concave element and bi-convex element with said concave side of said plano-concave element adjacent to said bi-convex element;

g) a sequential combination of a plano-convex element and a bi-concave element with said essentially flat side of said plano-convex element adjacent to said bi-concave element;

h) a sequential combination of a bi-concave element with a plano-convex element with said convex side of said plano-convex element adjacent to said bi-concave element;

i) a sequential combination of a plano-concave element and a plano-convex element with the essentially flat side of said plano-concave element being adjacent to the convex side of the plano-convex element;

j) a sequential combination of a plano-concve element and a plano-convex element with the essentially flat side of said planoconcave element being adjacent to the convex side of said plano-convex element;

k) a sequential combination of a plano-convex element and a plano-concave element with the essentially flat side of said plano-covex element and the essentially flat side of said plano-concave element being adjacent to one another;

l) a sequential combination of a plano-concave element and a plano-convex element with the concave side of said plano-concave element being adjacent to the convex side of the plano-convex element;

m) a sequential combination of a plano-convex element and a bi-concave element with said convex side of said plano-convex element adjacent to said bi-concave element;

n) a sequential combination of a bi-concave element and a plano-convex element with said essentially flat side of said plano-convex element adjacent to said bi-concave element;

o) a sequential combination of a plano-convex element and a plano-concave element with said convex side of said plano-convex element adjacent to the concave side of the plano-concave element;

p) a sequential combination of a plano-concave element and a plano-convex element with said essentially flat side of said plano-convex element being adjacent to the essentially flat side of the plano-concave element;

q) a sequential combination of a plano-convex element and a plano-concave element with said convex side of said plano-convex element being adjacent to the essentially flat side of the plano-concave element; and r) a sequential combination of a plano-concave element with a plano-convex element with the essentially flat side of said plano-convex element being adjacent to the concave side of said plano-concave element;

and wherein said region between said first and second elements having essentially the optical properties of a selection from the group consisting of:
  a void region; and
  a functional equivalent to a void region.

A present invention lens system with application in ellipsometer systems can be further characterized in that the converging element of said first and second elements is typically made of a material independently selected from the group consisting of:
  CaF
  $BaF_2$;
  LiF; and
  $MgF_2$;

and the diverging element of said first and second elements is selected to be made of fused silica, although it is within the scope of the present invention to make the converging element of fused silica and the diverging element of a selection from the group consisting of $CaF_2$; $BaF_2$; LiF; and $MgF_2$. It is noted that lens elements made of $MgF_2$ are typically bi-refringent whereas lens elements made of $CaF_2$; $BaF_2$ and LiF typically demonstrate far less bi-refringence, unless subjected to stress.

A present invention lens system with a focal length of fifty millimeters or less, with application in ellipsometer systems, can be described as being comprised of lens system comprising two sequentially oriented lenses, each of said sequentially oriented lenses being comprised of:
  at least two sequentially oriented elements, one of said at least two sequentially oriented elements being of a shape and orientation which individually converges a beam of electromagnetic radiation caused to pass therethrough, and the other being of a shape and orientation which individually diverges a beam of electromagnetic radiation caused to pass therethrough, there being a region between said first and second elements such that, in use, a beam of electromagnetic radiation sequentially passes through said first element, then said region therebetween, and then said second element before emerging as a focused beam of electromagnetic radiation; said lens system being described by a selection, as shown in FIGS. 1x–1zz, from the group consisting of:
  1. a sequential combination of a converging element (C), a diverging element (D), a converging element (C) and a diverging element (D);
  2. a sequential combination of a converging element (C), a diverging (D) element, a diverging (D), element and a converging (C) element;
  3. a sequential combination of a diverging element (D), a converging element (C), a diverging (D) element and a converging (C) element;
  4. a sequential combination of a diverging element (D), a converging element (C), a converging element (C) and a diverging (D) element.

And, of course, other sequential lens element configurations within the scope of the present invention include:
  (Converging(C))(Converging(C))(Diverging(D));
  (Diverging(D))(Diverging(D))(Converging(C));
  (Converging(C))(Diverging(D))(Diverging(D));
  (Diverging(D))(Converging(C))((Diverging(D));
  (Converging(C))(Converging(C))(Diverging(D))(Diverging(D)); and
  (Diverging(D))(Diverging(D))(Converging(C))(Converging(C)).

Specific embodiments of a present invention lens system is further characterized by at least one selection from the group consisting of:
  a. the focal length of the lens system is between forty (40) and forty-one (41) millimeters over a range of wavelengths of at least two-hundred (200) to seven-hundred (700) nanometers; and
  b. the focal length of the dual stage lens system varies by less than five (5%) percent over a range of wavelengths of between two-hundred and five-hundred nanometers; and
  c. the spot diameter at the focal length of the lens system is less than seventy-five (75) microns over a range of wavelengths of at least two-hundred (200) to seven-hundred (700) nanometers.

At least one of said input and output lenses, when selected and present, can demonstrate properties selected from the group consisting of:
  both demonstrating birefringence;
  neither demonstrating birefringence;
  one demonstrating birefringence and the other not.

Representative materials from which different elements in said input and output lenses can be made made are calcium fluoride (FE1) (FE1a) (FE1b), and fused silica (FE3), (FE3a) (FE3b).

Figure 2A:
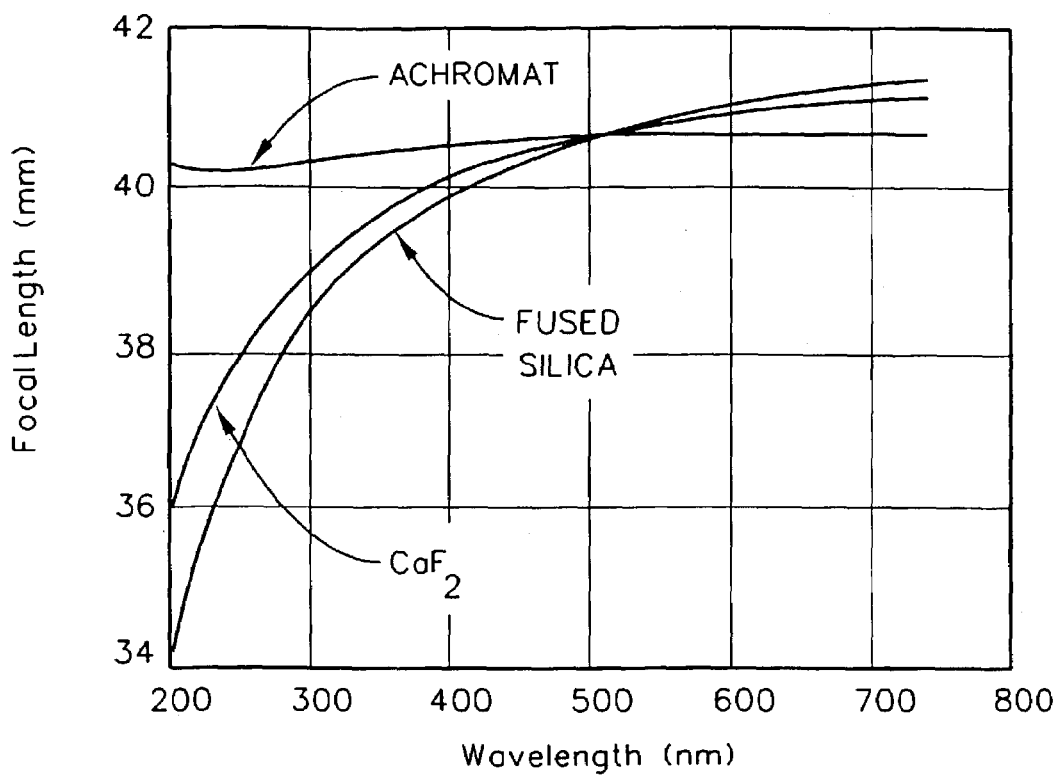
FIGS. 2a and 2b show focal length vs. wavelengths for various lens types, including quasi-achromatic lenses.
Figure 2B:
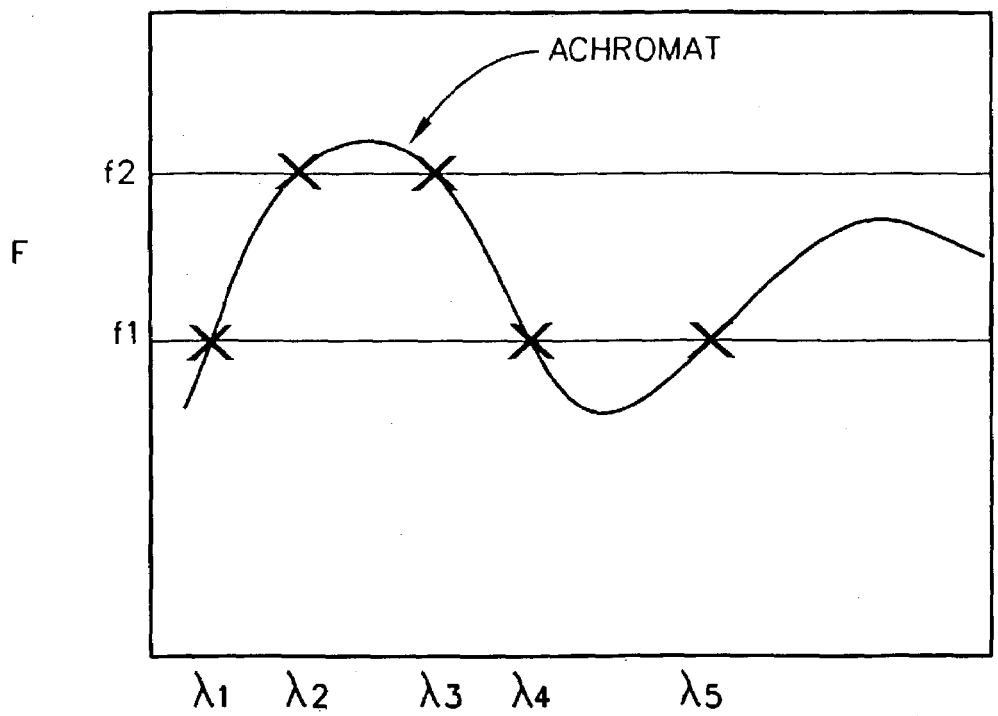

FIG. 2a shows an actual Focal Length vs. Wavelength plot for a multiple element lens. FIG. 2b is included to show that where a cyclic variation exists in Focal Length vs. Wavelength, it is possible to identify at least two Wavelengths ($\lambda 2$) and ($\lambda 3$) where the Focal Lengths (f2) are exactly equal. In some cases the Focal Lengths (f1) will be exactly the same at three wavelengths ($\lambda 1$), ($\lambda 4$) and ($\lambda 5$). Note that at ($\lambda 1$) an ($\lambda 4$) one focal length (f1) exists, and at that at ($\lambda 2$) and ($\lambda 3$) a second focal length exists. This gives insight that moving a single lens toward or away from a sample can cause different wavelengths to be selected at which the focal lengths are equal. Thus one embodiment of the invention allows for such lens motion as a means for enabling more than two wavelengths to investigate the same single spot on a sample. This is indicated in FIG. 3a2.

Figure 3B:
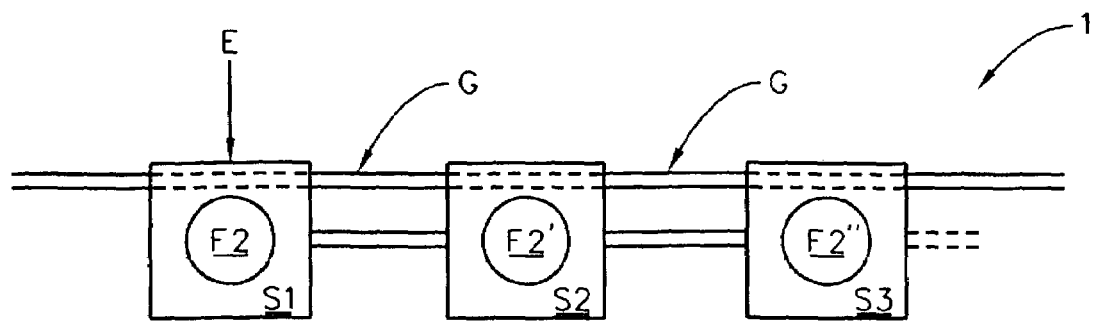
FIGS. 3b and 3c demonstrate slidable multiple input/output lens combinations.

Continuing, FIG. 3a1 demonstrates a simplified diagram showing an Electromagnetic beam (E) passing through a Converging Lens (F1), impinging on a Sample System (SS) and being recollimated by Lens (F2). FIG. 3b demonstrates that a system can be constructed to allow positioning a sequence of (S1), (S2) (S3) Systems which each contain Lens Systems (F1) (F2), (F1') (F2') and (F1") (F2"), (with F2, F2' and F2" being shown), into the pathway of the electromagnetic beam (E). A Guide (G) is shown along which the sequence of (S1), (S2) (S3) Systems can slide, which in FIG. 3a1 is into and out of the plane of the paper.

FIG. 3a2 indicates that a system can be constructed to allow moving a single lens toward or away form a sample. As described with respect to FIG. 2b, this can enable achieving more than two wavelengths which investigate the same spot on a sample.

Figure 3C:
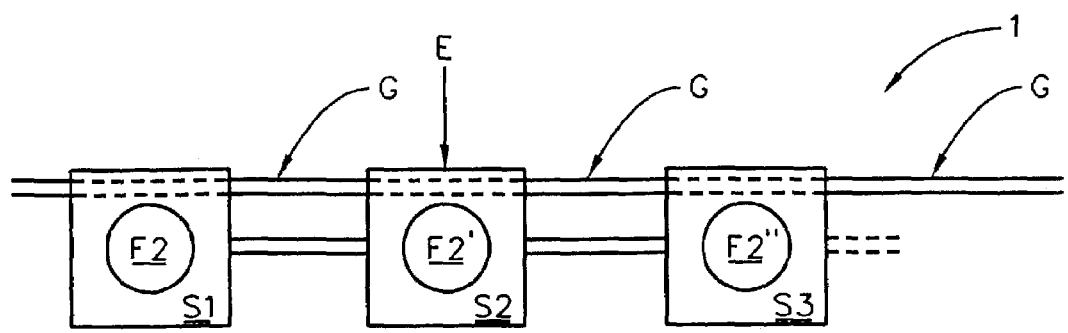

FIG. 3a3 shows another approach to providing a sequence of lenses (F1') (F1") and (F2) (F2') and (F2") into the beam (E) of electromagnetic radiation.

It should be appreciated that by limiting data utilized to that achieved at and/or in an acceptable range around wavelengths at which the focal lengths are substantially exactly the same in analysis, it is possible to characterize a sample at a very precise point location thereupon.

Further, where two wavelengths are insufficient to adequately characterize a sample at a single spot thereupon, it is possible to provide multiple lens sets which each provide the same focal length at at least two wavelengths, but which wavelengths are different from set to set.

It is to be understood that the term "Point" as utilized in this Specification is to be interpreted to mean that the areas a beam of electromagnetic radiation causes on a sample by two or more wavelengths therein, are concentric about substantially the same location upon said sample.

It is also to be understood that where a system of two lenses is referred to, it is means that one lens is prior to and another after a sample. It does not mean or require that one or both of said two lenses can not each be comprised of multiple lenses, or that one or both lenses can not be of multiple element construction.

Further, where it is stsated that a lens is placed at "a Focal Length" from a sample, said language is to be interpreted to include placement within practical deviations thereallround.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

The invention claimed is:

1. A method of analyzing a sample at substantially the exact same spot with at least two wavelengths of electromagnetic radiation, comprising the steps of:
practicing steps a and b in either order, said steps a and b being:
 a) providing a selection from the group consisting of:
  ellipsometer; and
  polarimeter;
which sequentially comprises a source of polychromatic electromagnetic radiation, a polarizer, a stage for supporting a sample, an analyzer and a detector;
 b) providing two refractive lens systems which have been designed to provide substantially the same focal length at two wavelengths;
 c) placing one of said refractive lens systems provided in step b prior to a sample which is positioned on said stage for supporting a sample, and one of said refractive lens systems after said sample, each of said refractive lens systems being placed substantially a focal length distance from a specific point on said sample;
 d. causing polychromatic electromagnetic radiation from said source thereof to pass through said polarizer and become focused onto said sample by said refractive lens system which is placed prior to said sample, such that said two wavelengths are focused onto said sample at substantially exactly the same point thereupon, then pass through said analyzer and enter said detector;
 e) utilizing only data provided by said detector that is obtained at said two wavelengths for which the focal length distances are substantially the same, in sample analysis.

2. A method of analyzing a sample at substantially the exact same spot with at least two wavelengths of electromagnetic radiation as in claim 1, in which steps a–d are repeated using refractive lenses which are designed to provide substantially the same focal length distances, at least one of said two wavelengths being different from the two wavelengths provided by the refractive lenses provided in step b.

3. A method as in claim 1 in which the focal lengths of the two wavelengths vary less than 5% one to the another.

4. A method as in claim 1 in which the refractive lens systems are of multiple element constuction.

5. A system selected from the group consisting of:
 ellipsometer;
 polarimeter;
 spectrophotometer; and
 reflectometer;
which sequentially comprises a source of polychromatic electromagnetic radiation, a stage for supporting a sample and a detector;
said system being characterized by refractive lens systems which have been designed to provide focal lengths which are substantially exactly the same at two specified wavelengths, one of said refractive lens systems being placed prior to a sample which is positioned on said stage for supporting a sample, and one of said refractive lens systems after said sample, each of said refractive lens systems being placed substantially a focal length distance from a specific point on said sample.

6. A method as in claim 5 in which the refractive lens systems are of multiple element constuction.

7. A method as in claim 5 in which the substantially non-diffracting refractive lens systems are of multiple element constuction.

8. A method of analyzing a sample at substantially the exact same spot with at least two wavelengths of electromagnetic radiation, comprising the steps of:
 a) providing a system selected from the group consisting of:
  ellipsometer;
  polarimeter;
  spectrophotometer; and
  reflectometer;
which sequentially comprises a source of polychromatic electromagnetic radiation, a stage for supporting a sample and a detector;
 b) providing two substantially non-diffracting refractive lens systems which have been designed to provide substantially the same focal length at two wavelengths;
 c) placing one of said substantially non-diffracting refractive lens systems provided in step b prior to a sample which is positioned on said stage for supporting a sample, and one of said substantially non-diffracting refractive lens systems after said sample, each of said substantially non-diffracting refractive lens systems being placed substantially a focal length distance from a specific point on said sample;

d. causing polychromatic electromagnetic radiation from said source thereof to become focused onto said sample by said substantially non-diffracting refractive lens system which is placed prior to said sample, such that said two wavelengths are focused onto said sample at substantially exactly the same point thereupon, then reflect therefrom and enter said detector;

e) utilizing only data provided by said detector that is obtained at said two wavelengths for which the focal length distances are substantially the same, in sample analysis.

9. A method of analyzing a sample at substantially the exact same spot with at least two wavelengths of electromagnetic radiation as in claim 8, in which steps a–d are repeated using substantially non-diffractive refractive lenses which are designed to provide substantially the same focal lengths, at least one of said two wavelengths being different from the two wavelengths provided by the substantially non-diffractive refractive lenses provided in step b.

10. A method as in claim 8 in which the focal lengths of the two wavelengths vary less than 5% one to the another.

* * * * *